United States Patent
Hagen

(10) Patent No.: US 10,302,541 B2
(45) Date of Patent: May 28, 2019

(54) OIL DEBRIS MONITORING (ODM) USING ACTIVE VALVE CONFIGURATION CONTROL

(71) Applicant: United Technologies Corporation, Farmington, CT (US)

(72) Inventor: Gregory S. Hagen, Glastonbury, CT (US)

(73) Assignee: UNITED TECHNOLOGIES CORPORATION, Farmington, CT (US)

(*) Notice: Subject to any disclaimer, the term of this patent is extended or adjusted under 35 U.S.C. 154(b) by 156 days.

(21) Appl. No.: 15/264,637

(22) Filed: Sep. 14, 2016

(65) Prior Publication Data

US 2018/0073970 A1 Mar. 15, 2018

(51) Int. Cl.
*G01N 15/02* (2006.01)
*G01N 15/06* (2006.01)
(Continued)

(52) U.S. Cl.
CPC ....... *G01N 15/0606* (2013.01); *F01D 21/003* (2013.01); *F01D 21/10* (2013.01); *F01D 25/18* (2013.01); *F02C 7/06* (2013.01); *G01N 15/02* (2013.01); *G01N 27/74* (2013.01); *F05D 2220/32* (2013.01); *F05D 2260/607* (2013.01); *F05D 2260/80* (2013.01); *F05D 2260/98* (2013.01); *G01N 33/2888* (2013.01); *Y02T 50/675* (2013.01)

(58) Field of Classification Search
CPC .... G01N 15/0606; G01N 15/02; G01N 27/74; G01N 33/2888; F01D 21/003; F01D 25/18; F05D 2220/32

USPC .......................................................... 73/53.07
See application file for complete search history.

(56) References Cited

U.S. PATENT DOCUMENTS 5,604,441 A * 2/1997 Freese .................. G01N 27/221
324/663
8,816,674 B2 * 8/2014 Ukai .................. G01N 33/2835
324/204
(Continued)

FOREIGN PATENT DOCUMENTS

| EP | 0513957 A1 | 11/1992 |
|---|---|---|
| EP | 2014877 A2 | 1/2009 |
| WO | 2015047885 A1 | 4/2015 |

OTHER PUBLICATIONS

Search Report for European Application No. 17180904.9, Application Filing Date Jul. 12, 2017; dated Apr. 13, 2018, 6 pages.

*Primary Examiner* — Natalie Huls
*Assistant Examiner* — Monica S Young
(74) *Attorney, Agent, or Firm* — Cantor Colburn LLP

(57) ABSTRACT

A gas turbine engine, a method, and a system for detecting oil debris are provided. The gas turbine engine includes an oil debris monitor sensor configured to detects oil debris in an oil flow, and generate a sensor signal based on the detected oil debris, a controller configured to control the oil flow through the oil debris monitor sensor using a plurality of valves, and a signal processor configured to receive the sensor signal from the oil debris monitor and to receive a valve system configuration from the controller, the signal processor further configured to generates a health indicator based on the sensor signal and valve configuration.

18 Claims, 4 Drawing Sheets

(51) Int. Cl.
*G01N 27/74* (2006.01)
*F01D 21/00* (2006.01)
*F01D 25/18* (2006.01)
*F01D 21/10* (2006.01)
*F02C 7/06* (2006.01)
G01N 33/28 (2006.01)

(56) References Cited

U.S. PATENT DOCUMENTS

| | | | |
|---|---|---|---|
| 2006/0047403 A1* | 3/2006 | Volponi | F01D 17/02 |
| | | | 701/100 |
| 2009/0014245 A1* | 1/2009 | Shevchenko | F01D 21/10 |
| | | | 184/6.4 |
| 2010/0027006 A1* | 2/2010 | Hertens | G01F 1/667 |
| | | | 356/335 |
| 2014/0326225 A1* | 11/2014 | Shioda | F02C 6/12 |
| | | | 123/559.1 |
| 2016/0017747 A1* | 1/2016 | Parnin | F01D 25/20 |
| | | | 73/53.07 |
| 2017/0254794 A1* | 9/2017 | Nielsen | G01N 33/2858 |
| 2018/0024106 A1* | 1/2018 | Roman | G01N 33/2858 |
| | | | 356/318 |

* cited by examiner

OIL DEBRIS MONITORING (ODM) USING ACTIVE VALVE CONFIGURATION CONTROL

STATEMENT OF FEDERAL SUPPORT

This invention was made with Government support under Contract No. N00019-02-C-3003 awarded by the Navy. The government therefore has certain rights in this invention.

BACKGROUND

The subject matter disclosed herein generally relates to oil debris monitoring and, more particularly, to oil debris monitoring in an engine.

Oil debris can present in oil flowing through an engine system overtime for a number of different reasons. For example, as engine components in an engine system wear, particulate will present in the oil that is lubricating the engine system. Specifically, the particulate can be generated from engine component breakdown, a breakdown of the oil itself, environmental conditions that introduce contaminating particulate that becomes the oil debris, and/or any combination thereof.

In order to approximate the amount of oil debris, the oil can be configured to pass through an oil debris monitor than can approximate the amount of debris in the oil by monitoring different properties of the oil that passes through the oil debris monitor. However, the accuracy and consistency of the oil debris monitor is affected by the flow volatility of the oil. For example, the flow of oil is controlled and affected by multiple valves distributed throughout the engine system as well as changes in component arrangement that can be due to different usage states such as, for example, a start-up state, a selected throttle state, and a shutting down state. These states can also be called modes of operation of the engine. These modes of operation can change the flow rate of the oil which can change the detected properties that are being monitored.

Accordingly, there is a desire for improved accuracy of the oil debris monitoring.

BRIEF DESCRIPTION

According to one embodiment a gas turbine engine with oil debris monitoring is provided. The gas turbine engine includes an oil debris monitor sensor configured to detects oil debris in an oil flow, and generate a sensor signal based on the detected oil debris, a controller configured to control the oil flow through the oil debris monitor sensor using a plurality of valves, and a signal processor configured to receive the sensor signal from the oil debris monitor and to receive a valve system configuration from the controller, the signal processor further configured to generates a health indicator based on the sensor signal and valve configuration.

In addition to one or more of the features described above, or as an alternative, further embodiments may include, wherein the health indicator includes at least one of an estimated value of debris in the oil flow, a type of debris, a calculated size of debris particulate, and a calculated amount of debris in the oil over time.

In addition to one or more of the features described above, or as an alternative, further embodiments may include, wherein the signal processer receives health indicators over time, and detects and anomaly in the oil debris based on the health indicators over time.

In addition to one or more of the features described above, or as an alternative, further embodiments may include, wherein the signal processor receives information characterizing the valve system configurations history over time and detects the anomaly in the oil debris based on the valve system configurations over time and the health indicators over time.

In addition to one or more of the features described above, or as an alternative, further embodiments may include, wherein the oil debris monitor sensor is configured to detect oil debris by detecting one or more of at least a magnetic field and a disturbance to an expected magnetic field through the oil flow and to calculate an oil debris amount that corresponds to the magnetic field detected.

In addition to one or more of the features described above, or as an alternative, further embodiments may include, an oil flow bypass valve connected in parallel with the oil debris monitor sensor, and an oil flow regulator valve connected in series with the oil debris monitor sensor.

In addition to one or more of the features described above, or as an alternative, further embodiments may include, wherein the oil flow bypass valve is configured to adjust the oil flow through an oil flow bypass to control the flow of the oil flow through the oil debris monitor sensor, and wherein the oil flow regulator valve is configured to adjust the oil flow through an oil flow bypass to control the flow of the oil flow through the oil debris monitor sensor.

In addition to one or more of the features described above, or as an alternative, further embodiments may include, wherein the oil flow bypass valve is further configured to adjust flow through the bypass valve based on at least one of a temperature of oil, pressure of oil, quantity of oil, opening and closing of other valves from the plurality of valves, oil flow through the oil debris monitor sensor, mechanical load, mode of operation, and shaft speeds.

In addition to one or more of the features described above, or as an alternative, further embodiments may include, wherein the plurality of valves are configured to determine the oil flow through the oil debris monitor sensor, and wherein the controller is configured to adjust the valve system configuration using the control signals to control the plurality of valves to control the oil flow through the oil debris monitor sensor.

In addition to one or more of the features described above, or as an alternative, further embodiments may include, wherein the plurality of valves includes at least an actively controlled valve and a passively controlled valve.

In addition to one or more of the features described above, or as an alternative, further embodiments may include, wherein the actively controlled valve is driven by the controller in order to provide lubrication system performance to meet the needs of a current state of operation of the mechanical system.

In addition to one or more of the features described above, or as an alternative, further embodiments may include, wherein the passively controlled valve is configured to respond directly to the mechanical properties of the mechanical system.

In addition to one or more of the features described above, or as an alternative, further embodiments may include, wherein the passively controller valve is a pressure-driven bypass valves.

According to one embodiment a computer implemented method for oil debris monitoring in a gas turbine engine is provided. The method includes generating control signals to control an oil flow using a plurality of valves in response to a sensor signal indicating oil debris in the oil flow, receiving a valve system configuration, and generating, using a signal processor, a health indicator based on the sensor signal and the valve configuration.

In addition to one or more of the features described above, or as an alternative, further embodiments may include, wherein the health indicator includes at least one of an estimated value of debris in the oil flow, a type of debris, a calculated size of debris particulate, and a calculated amount of debris in the oil over time.

In addition to one or more of the features described above, or as an alternative, further embodiments may include, detecting, using the oil debris monitor sensor, oil debris by detecting one or more of at least a magnetic field and a disturbance to an expected magnetic field through the oil flow and calculating an oil debris amount that corresponds to the magnetic field detected.

In addition to one or more of the features described above, or as an alternative, further embodiments may include, adjusting, using at least one of an oil flow bypass valve and regulator valve, the oil flow through at least one of the oil flow bypass and regulator valve to control the flow of the oil flow through the oil debris monitor sensor.

In addition to one or more of the features described above, or as an alternative, further embodiments may include, adjusting, using an oil flow bypass valve, flow through the bypass valve based on at least one of a temperature of oil, pressure of oil, quantity of oil, opening and closing of other valves from the plurality of valves, oil flow through the oil debris monitor sensor, mechanical load, mode of operation, and shaft speeds.

In addition to one or more of the features described above, or as an alternative, further embodiments may include, wherein the plurality of valves determine the oil flow through the oil debris monitor sensor, and wherein the controller adjusts the valve system configuration using the control signals to control the plurality of valves to control the oil flow through the oil debris monitor sensor.

According to one embodiment a computer program product for oil debris monitoring in a gas turbine engine is provided. The computer program product including a computer readable storage medium having program instructions embodied therewith, the program instructions executable by a processor to cause the processor to generate control signals to control an oil flow using a plurality of valves in response to a sensor signal indicating oil debris in the oil flow, receive a valve system configuration, and generate a health indicator based on the sensor signal and the valve configuration.

BRIEF DESCRIPTION OF THE DRAWINGS

The foregoing and other features, and advantages of the present disclosure are apparent from the following detailed description taken in conjunction with the accompanying drawings in which.

DETAILED DESCRIPTION

Figure 1:
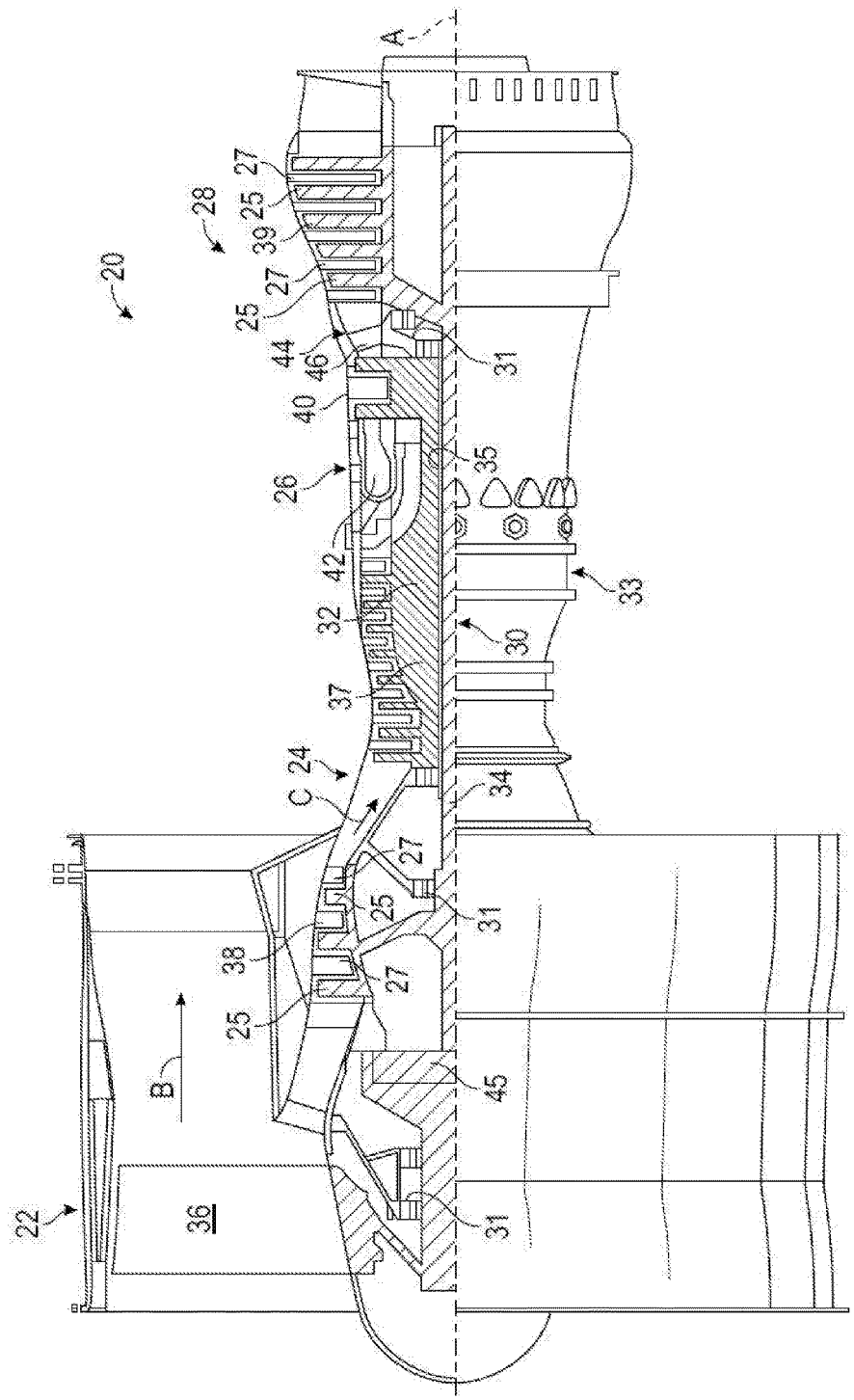
FIG. 1 is a schematic cross-sectional illustration of a gas turbine engine that may employ various embodiments disclosed herein.

As shown and described herein, various features of the disclosure will be presented. Various embodiments may have the same or similar features and thus the same or similar features may be labeled with the same reference numeral, but preceded by a different first number indicating the figure to which the feature is shown. Thus, for example, element "a" that is shown in FIG. X may be labeled "Xa" and a similar feature in FIG. Z may be labeled "Za." Although similar reference numbers may be used in a generic sense, various embodiments will be described and various features may include changes, alterations, modifications, etc. as will be appreciated by those of skill in the art, whether explicitly described or otherwise would be appreciated by those of skill in the art.

Embodiments described herein are directed to an engine system that includes one or more apparatus such as a bypass valve and engine debris monitor and a method for using such an apparatus, for detecting particles in engine oil debris monitoring (ODM) system. Additionally, according to one or more embodiments, the ODM system uses system configuration information to help tune the sensor signals in order to determine if there is debris in the oil. This tuning of the sensor signals based on the configuration information reduces false positives and negatives. Specifically, the ODM system can use the system configuration information to understand what portions of or sub-systems are under load and are most likely to be the ones generating the debris.

FIG. 1 schematically illustrates a gas turbine engine 20. The exemplary gas turbine engine 20 is a two-spool turbofan engine that generally incorporates a fan section 22, a compressor section 24, a combustor section 26, and a turbine section 28. Alternative engines might include an augmenter section (not shown) among other systems for features. The fan section 22 drives air along a bypass flow path B, while the compressor section 24 drives air along a core flow path C for compression and communication into the combustor section 26. Hot combustion gases generated in the combustor section 26 are expanded through the turbine section 28. Although depicted as a turbofan gas turbine engine in the disclosed non-limiting embodiment, it should be understood that the concepts described herein are not limited to turbofan engines and these teachings could extend to other types of engines, including but not limited to, three-spool engine architectures.

The gas turbine engine 20 generally includes a low speed spool 30 and a high speed spool 32 mounted for rotation about an engine centerline longitudinal axis A. The low speed spool 30 and the high speed spool 32 may be mounted relative to an engine static structure 33 via several bearing systems 31. It should be understood that other bearing systems 31 may alternatively or additionally be provided.

The low speed spool 30 generally includes an inner shaft 34 that interconnects a fan 36, a low pressure compressor 38 and a low pressure turbine 39. The inner shaft 34 can be connected to the fan 36 through a geared architecture 45 to drive the fan 36 at a lower speed than the low speed spool 30. The high speed spool 32 includes an outer shaft 35 that interconnects a high pressure compressor 37 and a high pressure turbine 40. In this embodiment, the inner shaft 34 and the outer shaft 35 are supported at various axial locations by bearing systems 31 positioned within the engine static structure 33.

A combustor 42 is arranged between the high pressure compressor 37 and the high pressure turbine 40. A mid-turbine frame 44 may be arranged generally between the high pressure turbine 40 and the low pressure turbine 39. The mid-turbine frame 44 can support one or more bearing systems 31 of the turbine section 28. The mid-turbine frame 44 may include one or more airfoils 46 that extend within the core flow path C.

The inner shaft 34 and the outer shaft 35 are concentric and rotate via the bearing systems 31 about the engine centerline longitudinal axis A, which is co-linear with their longitudinal axes. The core airflow is compressed by the low pressure compressor 38 and the high pressure compressor 37, is mixed with fuel and burned in the combustor 42, and is then expanded over the high pressure turbine 40 and the low pressure turbine 39. The high pressure turbine 40 and the low pressure turbine 39 rotationally drive the respective high speed spool 32 and the low speed spool 30 in response to the expansion.

Each of the compressor section 24 and the turbine section 28 may include alternating rows of rotor assemblies and vane assemblies (shown schematically) that carry airfoils that extend into the core flow path C. For example, the rotor assemblies can carry a plurality of rotating blades 25, while each vane assembly can carry a plurality of vanes 27 that extend into the core flow path C. The blades 25 of the rotor assemblies create or extract energy (in the form of pressure) from the core airflow that is communicated through the gas turbine engine 20 along the core flow path C. The vanes 27 of the vane assemblies direct the core airflow to the blades 25 to either add or extract energy.

Further, one or more of the engine components as shown use oil that flows in and/or around the components that is used to lubricate the components' movements as well as provide heat dissipation to help control engine component temperatures. The oil can be provided to the engine by an oil pump and valve system that also includes an oil flow controller. Additionally one or more sensors, such as an oil debris monitor, can be included to collect information about the oil that can indicate both the condition of the oil and also the condition of different components of the engine.

Particularly, engine lubricating oils are routinely monitored for the detection of possible particles, which may be early indications of component failure such as failures of the gearbox and bearing components for example. Manual routine inspection can be complex and time-consuming. According to one or more embodiments, condition-based maintenance and monitoring systems rely on sensor systems. Further, according to one or more embodiments, sensor systems are used to automatically detect particles in the lubricating system. However, robust particle detection can be challenging as the sensor signal characteristics may differ under various engine operating conditions and various signal noise levels. In addition, each engine may have its own ODM signal profiles due to its unique sensor and installation characteristics. Although perfect particle signal characteristics in a lab environment are well-known, detecting particles in an operational production environment requires well-designed detection methods that can be adapted to various engine operating conditions.

One or more embodiments of the present disclosure features an apparatus and/or associated method for optimizing mechanical system failure debris detection that utilizes knowledge of the system's configuration settings to optimize signal processing algorithms to produce more accurate debris detection features. One or more embodiments include an oil debris monitor sensor. According to other embodiments, the system's configuration settings include, for example, state indicators of various valve settings, lubrication fluid temperatures, and pressures.

Furthermore, according to one or more embodiments, knowledge of the configuration can be utilized to tune health indicator thresholds based in part on knowledge of the specific loadings of each of the components and their associated failure modes. Particularly, according to one or more embodiments, the ODM system can use system configuration information to help tune not only the health indicator thresholds but the sensor signals as well in order to determine if there is debris in the oil. This tuning of the health thresholds and sensor signals based on the configuration information reduces false positives and negatives. Further, the ODM system can use the system configuration information to understand what portions of the system or sub-systems are under load and are most likely to be the ones generating the debris.

Figure 2:
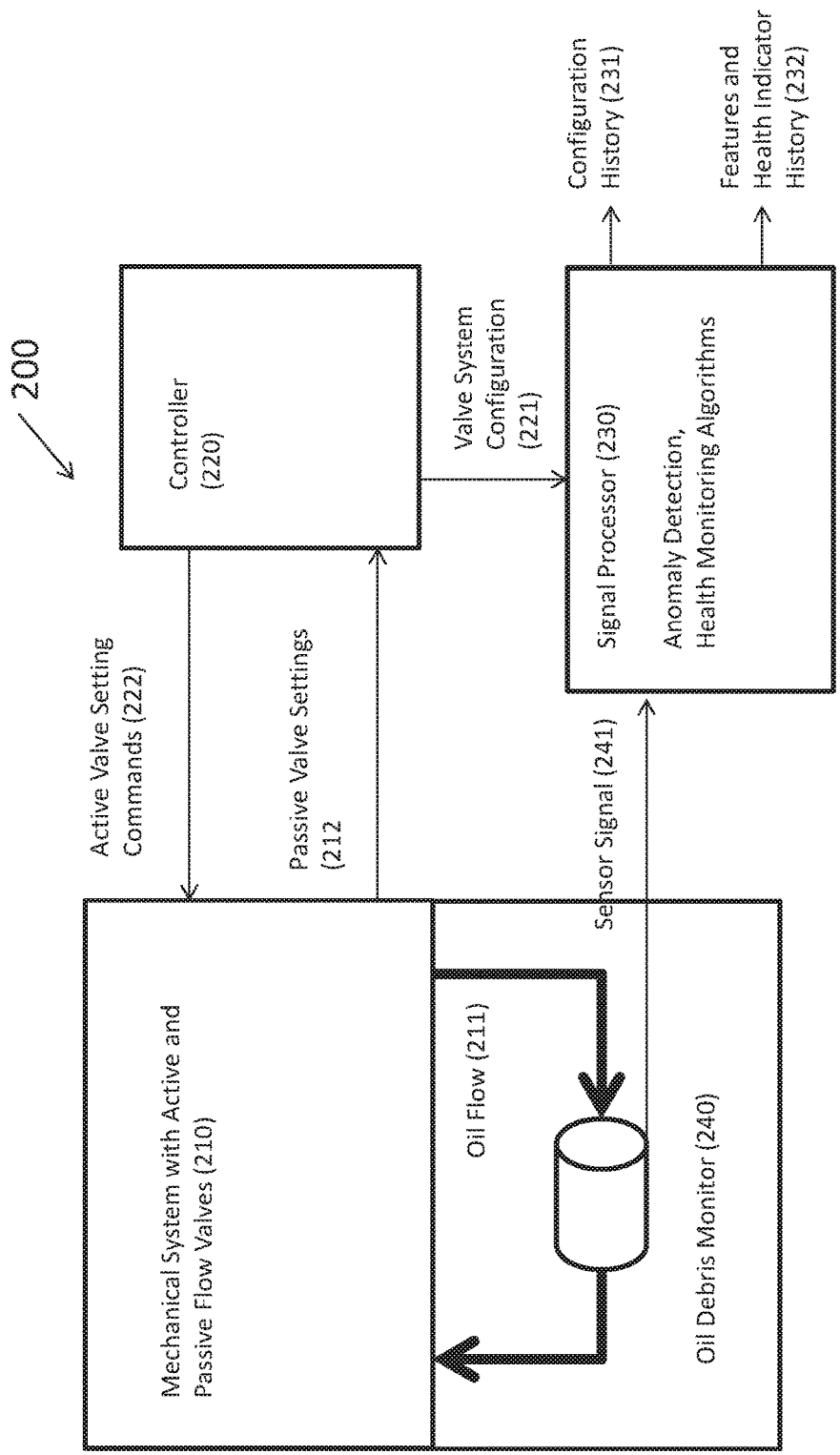
FIG. 2 is a block diagram of an engine system that includes an oil debris monitor in accordance with one or more embodiments of the present disclosure.

For example, turning now to FIG. 2, a gas turbine engine system 200 is shown in accordance with one or more embodiments. The gas turbine engine system 200 includes a mechanical system 210, such as the components shown in FIG. 1 of the gas turbine engine. The mechanical system 210 includes active and passive flow valves. The system 200 also includes an oil debris monitor 240 through which a particular oil flow 211 is provided from one or more of the components of the mechanical system 210. Further, the system 200 includes a controller 220 and a signal processor 230.

The controller 220 generates and provides commands to the mechanical system 210 and configuration information to the signal processor 230. For example, the controller 220 can specifically provide active valve setting commands 222 to the mechanical system 210. The mechanical system 210 can in turn provide passive valve settings 212 back to the controller 220. Additionally, the oil debris monitor 240 can provide a sensor signal 241 to the signal processor 230. The signal processor 230 can provide anomaly detection using the received sensor signal 241 and one or more health monitoring algorithms contained therewith. Further, the signal processor 230 can also provide configuration history 231. Additionally, the signal processor 230 can processes the received sensor signal 241 and any other signals that are received to detect features and health indicators of different components based on what is detected in the oil flow 211 through the oil debris monitor 240.

In accordance with one or more embodiments, the controller 220 provides specific active valve setting commands 222 that not only accomplish whatever the mechanical system and overall engine system desire, but can also be adjusted such that one or more of the active valves in the mechanical system 210 are adjusted to provide a consistent oil flow 211 to the oil debris monitor 240. By providing the consistent oil flow 211 by adjusting one or more valves the sensor signal 241 can be processed by the signal processor 230 for system features and health indicator values that are more accurate since the flow is known and consistent.

Figure 3:
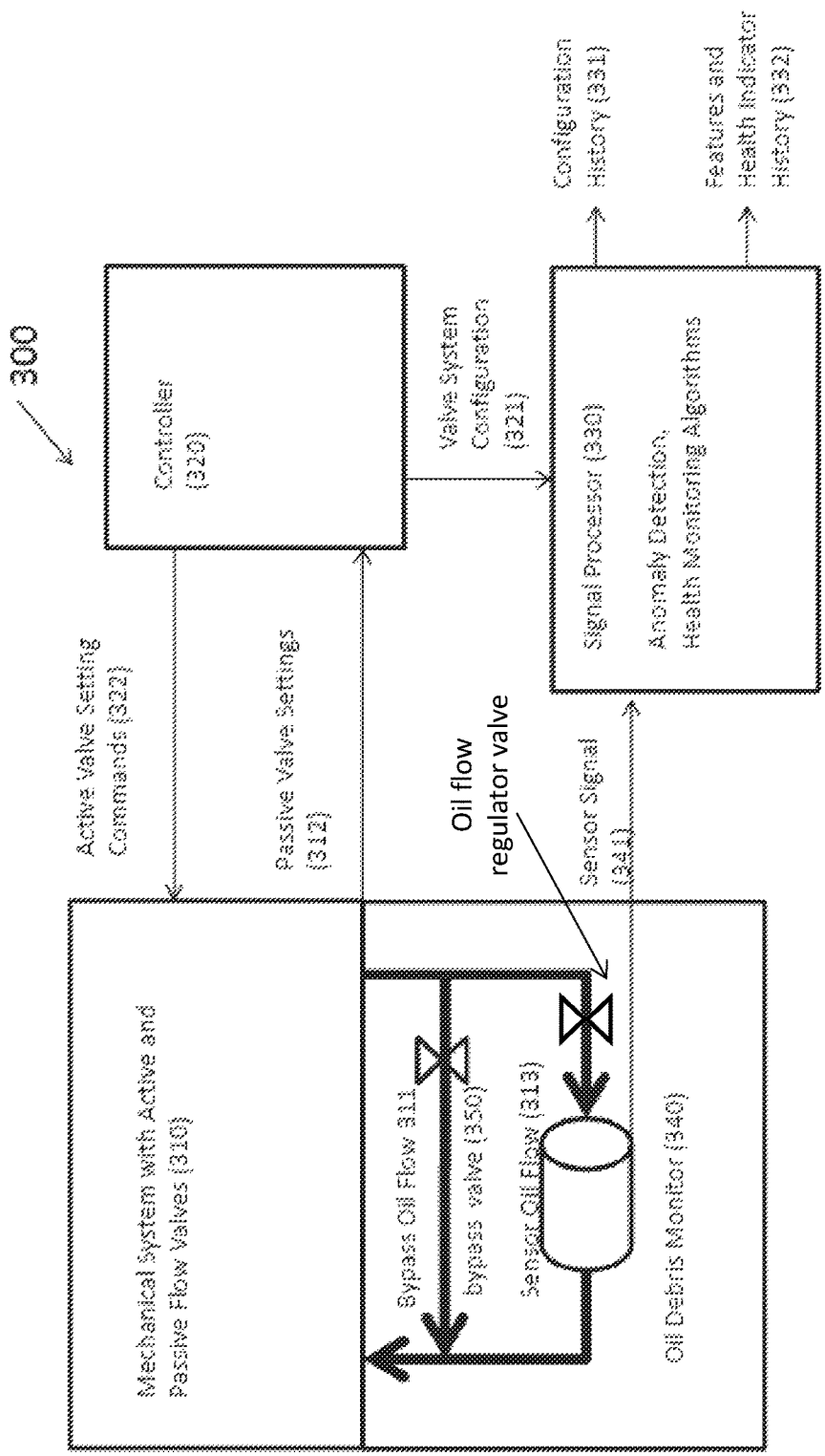
FIG. 3 is a block diagram of an engine system that includes an oil debris monitor and a bypass valve in accordance with one or more embodiments of the present disclosure.

According to other embodiments, FIG. 3 depicts is a block diagram of a engine system 300 that includes at least an oil debris monitor 340 and a bypass valve 350 in accordance with one or more embodiments of the present disclosure.

Specifically, the gas turbine engine system 300 includes a mechanical system 310, such as the components shown in FIG. 1 of the gas turbine engine. The mechanical system 310 includes active and passive flow valves. The system 300 also includes an oil debris monitor 340 through which a particular sensor oil flow 313 is provided from one or more of the components of the mechanical system 310. Further, the system 200 includes a controller 320 and a signal processor 330.

The controller 320 generates and provides commands to the mechanical system 310 and configuration information to the signal processor 330. For example, the controller 320 can specifically provide active valve setting commands 322 to the mechanical system 310. The mechanical system 310 can in turn provide passive valve settings 312 back to the controller 320. Additionally, the oil debris monitor 340 can provide a sensor signal 341 to the signal processor 330. The signal processor 330 can provide anomaly detection using the received sensor signal 341 and one or more health monitoring algorithms contained therewith. Further, the signal processor 330 can also provide configuration history 331 of the valve over time. Additionally, the signal processor 330 can processes the received sensor signal 341 and any other signals that are received to detect features and health indicator of different components based on what is detected in the oil flow 311 through the oil debris monitor 340.

In accordance with one or more embodiments, the bypass valve 350 can be adjusted such that a consistent sensor oil flow 313 can be provided to the oil debris monitor 340. Specifically, the consistent oil flow 313 can be provided by adjusting the bypass oil flow 311 to compensate for any changes in the oil flow caused by the mechanical system with active and passive valves. The sensor signal 341 can be processed by the signal processor 330 for system features and health indicator values that are more accurate since the sensor oil flow 313 is known and consistent.

For example, the specific type and amount of particulate can be detected in the oil that is flowing by at a consistent rate during one or more modes of operation. This material can sometimes be identified as originating from a specific element/device in the engine system. Further, the existence of a particular quantities of particles can indicate a particular wear condition of the component.

Figure 4:
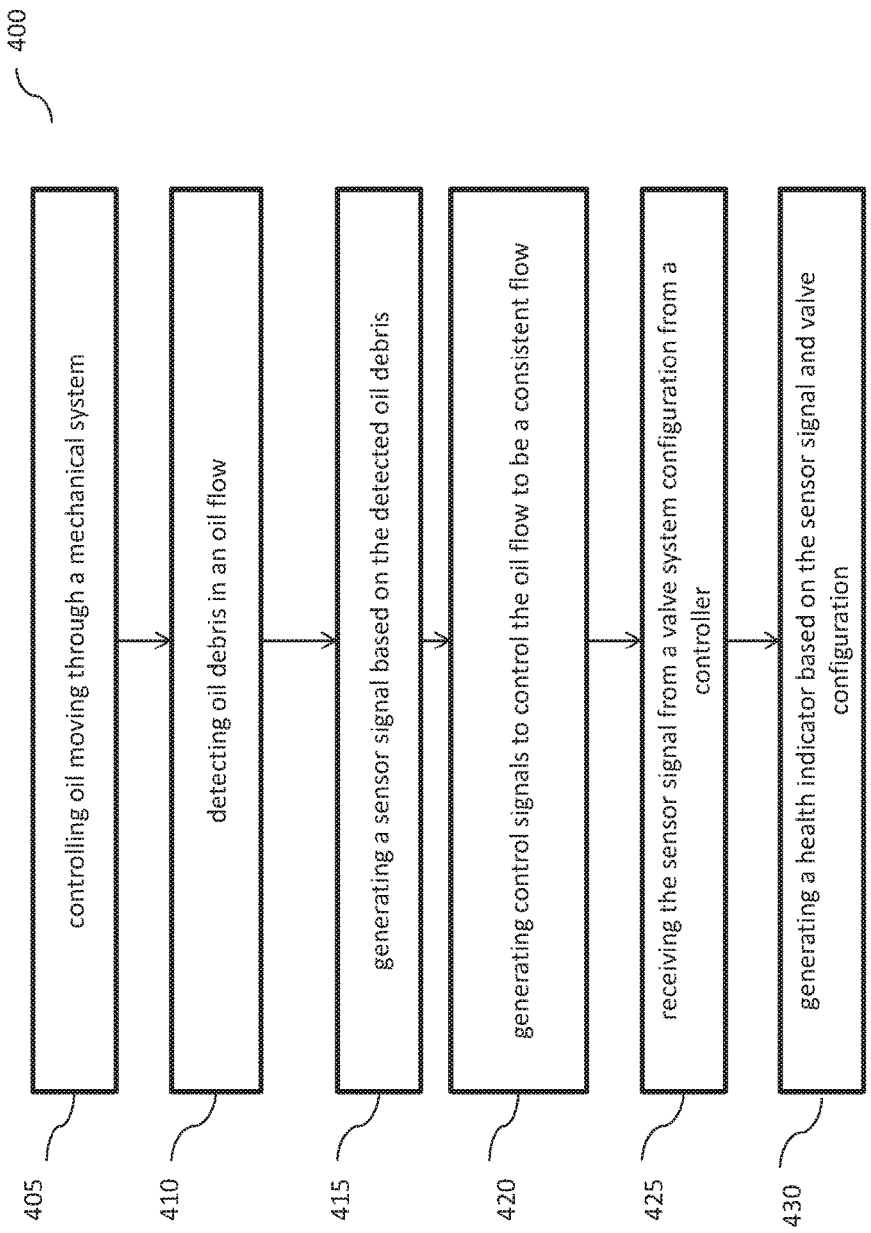
FIG. 4 is a flowchart of a method for monitoring oil debris in accordance with one or more embodiments of the present disclosure.

According to one or more embodiments, a method for monitoring oil debris can include generating control signals to control an oil flow using a plurality of valves in response to a sensor signal indicating oil debris in the oil flow. The method can also include receiving a valve system configuration, and generating, using a signal processor, a health indicator based on the sensor signal and the valve configuration FIG. 4 is a flowchart of a method 400 for monitoring oil debris in accordance with one or more embodiments of the present disclosure. The method 400 includes controlling oil moving through a mechanical system (operation 405). According to an embodiment, controlling oil moving through the mechanical system is done using a plurality of valves. The method 400 also includes detecting, oil debris in an oil flow (operation 410). According to an embodiment, an oil debris monitor sensor may be used to detect oil debris in an oil flow. In another embodiment the oil flow is from the mechanical system. The method further includes generating a sensor signal based on the detected oil debris (operation 415). According to an embodiment, an oil debris monitor sensor may be used to generate the sensor signal based on the detected oil debris. The method also includes generating control signals to control the oil flow be a consistent flow through the oil debris monitor sensor (operation 420). According to an embodiment, the oil flow is held consistent through the oil debris monitor sensor. According to an embodiment, an oil debris monitor may generate control signals to control the oil flow by controlling a plurality of valves. The method 400 also includes receiving the sensor signal from a valve system configuration from the controller (operation 425). According to an embodiment, the method receives the sensor signal from the oil debris monitor and the valve system configuration from the controller. According to an embodiment, the sensor signal from the oil debris monitor and valve system configuration is received at a signal processor. The method further includes generating, a health indicator based on the sensor signal and valve configuration (operation 430). According to an embodiment, the signal process generate the health indicator based on the sensor signal and valve configuration.

Further, according to one or more embodiments, an apparatus and associated method for optimizing mechanical system failure debris detection is based on knowledge of the operational state of the machine, which in turn dictates which components are actively loaded and have a higher likelihood of exhibiting failure symptoms. The apparatus features a lube system with both actively and passively controlled valves. Actively controlled valves are driven by the system controls in order to provide lubrication system performance to meet the needs of the machine's current state of operation. Passively controlled valves, such as pressure-driven bypass valves, respond directly to the oil systems mechanical properties. The configuration state of the system is determined by the control system, either through direct commands for active valves or oil pressure and temperature measurements for passive valves. The control system uses this information to optimize signal processing algorithms (e.g. tuning based on time scales, frequencies, lubrication properties such as temperature and pressure) to more accurately detect signal features associated with mechanical system failure debris and to more effectively calculate health indicators that are customized to the specific failure modes associate with the components that are more heavily loaded and therefore more likely to fail.

According to one or more embodiments, a gas turbine engine with oil debris monitoring includes at least an oil debris monitor sensor configured to detects oil debris in an oil flow. The oil debris monitor sensor can also generate a sensor signal based on the detected oil debris. The gas turbine engine also includes a controller configured to control the oil flow through the oil debris monitor sensor using a plurality of valves. Also included is a signal processor configured to receive the sensor signal from the oil debris monitor and to receive a valve system configuration from the controller, the signal processor further configured to generates a health indicator based on the sensor signal and valve configuration.

According to one or more embodiments, the health indicator includes at least one of an estimated value of debris in the oil flow, a type of debris, a calculated size of debris particulate, and a calculated amount of debris in the oil over time. According to one or more embodiments, the signal processer receives health indicators over time, and detects and anomaly in the oil debris based on the health indicators over time. According to one or more embodiments, the signal processor receives information characterizing the valve system configurations history over time and detects the anomaly in the oil debris based on the valve system configurations over time and the health indicators over time.

According to one or more embodiments, the oil debris monitor sensor is configured to detect oil debris by detecting one or more of at least a magnetic field and a disturbance to an expected magnetic field through the oil flow and to calculate an oil debris amount that corresponds to the magnetic field detected. According to one or more embodiments, the plurality of valves further includes an oil flow bypass valve connected in parallel with the oil debris monitor sensor, and an oil flow regulator valve connected in series with the oil debris monitor sensor.

According to one or more embodiments, the oil flow bypass valve adjusts the oil flow through an oil flow bypass to control the flow of the oil flow through the oil debris monitor sensor. According to one or more embodiments, the oil flow regulator valve adjusts the oil flow through an oil flow bypass to control the flow of the oil flow through the oil debris monitor sensor. According to one or more embodiments, the oil flow bypass valve is further configured to adjust flow through the bypass valve based on at least one of a temperature of oil, pressure of oil, quantity of oil, opening and closing of other valves from the plurality of valves, oil flow through the oil debris monitor sensor, mechanical load, mode of operation, and shaft speeds.

According to one or more embodiments, the plurality of valves determines the oil flow through the oil debris monitor sensor. Further, according to one or more embodiments, the controller adjusts the valve system configuration using the control signals to control the plurality of valves to control the oil flow through the oil debris monitor sensor.

According to one or more embodiments, the plurality of valves includes at least an actively controlled valve and a passively controlled valve. According to one or more embodiments, the actively controlled valve is driven by the controller in order to provide lubrication system performance to meet the needs of a current state of operation of the mechanical system. According to one or more embodiments, the passively controlled valve responds directly to the mechanical properties of the mechanical system. According to one or more embodiments, the passively controller valve is a pressure-driven bypass valves.

In accordance with one or more embodiments, potential applications include, but are not limited to, the following examples:

In a vertical lift propulsion system, a lift fan mechanical system is engaged during powered lift. These configurations exhibit different flow rates through the oil debris monitor and result in different mechanical loadings on components in the system. Health indicators can be specifically defined for the different failure modes associated with each mode of operation. Furthermore, oil temperatures change during the different modes of operation. Accordingly having a bypass valve can provide the control needed to stabilize the flow through the debris sensor.

Specifically, in one or more embodiments, an actively controlled bypass valve can be utilized to maintain a constant flow rate through the oil debris monitor. This allows the signal processing to be optimized for a more narrow range of flow rates.

In one or more embodiments, oil filter bypass valves may open when the filter gets clogged. This exposes the components to a higher risk of failure and may result in higher oil temperatures.

In one or more embodiments, thermal management systems may exhibit switching behavior that modifies the oil flow rates and temperatures throughout the system.

In accordance with one or more embodiments, at least one embodiment allows the signal processing to be more accurate by allowing a very narrow range of signal wavelengths to indicate debris.

Further, one or more embodiments allow the health indicators to be more accurately by specifically identifying which components are loaded during different modes of operation and assigning thresholds to produce failure detection capability more closely aligned with safety and reliability requirements.

While the present disclosure has been described in detail in connection with only a limited number of embodiments, it should be readily understood that the present disclosure is not limited to such disclosed embodiments. Rather, the present disclosure can be modified to incorporate any number of variations, alterations, substitutions, combinations, sub-combinations, or equivalent arrangements not heretofore described, but which are commensurate with the scope of the present disclosure. Additionally, while various embodiments of the present disclosure have been described, it is to be understood that aspects of the present disclosure may include only some of the described embodiments.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description has been presented for purposes of illustration and description, but is not intended to be exhaustive or limited to the embodiments in the form disclosed. Many modifications and variations will be apparent to those of ordinary skill in the art without departing from the scope of the disclosure. The embodiments were chosen and described in order to best explain the principles of the disclosure and the practical application, and to enable others of ordinary skill in the art to understand various embodiments with various modifications as are suited to the particular use contemplated.

The present embodiments may be a system, a method, and/or a computer program product at any possible technical detail level of integration. The computer program product may include a computer readable storage medium (or media) having computer readable program instructions thereon for causing a processor to carry out aspects of the present disclosure.

Aspects of the present invention are described herein with reference to flowchart illustrations and/or block diagrams of methods, apparatus (systems), and computer program products according to embodiments. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The flowchart and block diagrams in the Figures illustrate the architecture, functionality, and operation of possible implementations of systems, methods, and computer program products according to various embodiments. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Accordingly, the present disclosure is not to be seen as limited by the foregoing description, but is only limited by the scope of the appended claims.

What is claimed is:

1. A gas turbine engine with oil debris monitoring comprising:
    an oil debris monitor sensor configured to detect oil debris in an oil flow, and generate a sensor signal based on the detected oil debris;
    a controller configured to control the oil flow through the oil debris monitor sensor using a plurality of valves; and
    a signal processor configured to receive the sensor signal from the oil debris monitor and to receive a valve system configuration from the controller indicating a load applied to the plurality of valves, the signal processor further configured to generate a health indicator based on the detected oil debris indicated by the sensor signal and the load indicated by the valve system configuration,
    wherein the plurality of valves further comprises:
        a bypass oil flow path that bypasses the oil debris monitor sensor;
        an oil flow bypass valve connected in parallel with the oil debris monitor sensor, the oil flow bypass valve configured to control an amount of oil that flows through the bypass oil flow path; and
        an oil flow regulator valve connected in series with the oil debris monitor sensor, the oil flow regulator valve configured to control an amount of input oil flow delivered to the oil debris monitor sensor.

2. The gas turbine engine with oil debris monitoring of claim 1,
    wherein the health indicator includes at least one of an estimated value of debris in the oil flow, a type of debris, a calculated size of debris particulate, and a calculated amount of debris in the oil over time.

3. The gas turbine engine with oil debris monitoring of claim 1,
    wherein the signal processer receives health indicators over time, and detects an anomaly in the oil debris based on the health indicators over time.

4. The gas turbine engine with oil debris monitoring of claim 3,
    wherein the signal processor receives information characterizing the valve system configurations history indicating valve settings over time and detects the anomaly in the oil debris based on the valve system configurations over time and the health indicators over time.

5. The gas turbine engine with oil debris monitoring of claim 1,
    wherein the oil debris monitor sensor is configured to detect oil debris by detecting one or more of at least a magnetic field and a disturbance to an expected magnetic field through the oil flow and to calculate an oil debris amount that corresponds to the magnetic field detected.

6. The gas turbine engine with oil debris monitoring of claim 1, wherein, in response to actively opening and closing the oil flow bypass valve to adjust the oil flow through the oil flow bypass, an amount of input oil flow delivered to the oil flow regulator valve is varied to maintain a constant flow rate of the oil flow through the oil debris monitor sensor, and wherein the oil flow regulator valve is configured to adjust the oil flow through an oil flow bypass to control the oil flow through the oil debris monitor sensor.

7. The gas turbine engine with oil debris monitoring of claim 1, wherein the oil flow bypass valve is further configured to adjust flow through the bypass valve based on at least one of a temperature of oil, pressure of oil, quantity of oil, opening and closing of other valves from the plurality of valves, oil flow through the oil debris monitor sensor, mechanical load, mode of operation, and shaft speeds.

8. The gas turbine engine with oil debris monitoring of claim 1,
    wherein the plurality of valves are configured to determine the oil flow through the oil debris monitor sensor, and
    wherein the controller is configured to adjust the valve system configuration using the control signals to control the plurality of valves to control the oil flow through the oil debris monitor sensor.

9. The gas turbine engine with oil debris monitoring of claim 1,
    wherein the plurality of valves includes at least an actively controlled valve and a passively controlled valve.

10. The gas turbine engine with oil debris monitoring of claim 9,
    wherein the actively controlled valve is driven by the controller in order to provide lubrication system performance to invoke a current state of operation of the mechanical system.

11. The gas turbine engine with oil debris monitoring of claim 9,
wherein the passively controlled valve is configured to respond directly to the mechanical properties of the mechanical system.

12. The gas turbine engine with oil debris monitoring of claim 11, wherein the passively controlled valve is a pressure-driven bypass valve.

13. A computer implemented method for oil debris monitoring in a gas turbine engine, the method comprising:
generating control signals to control an oil flow using a plurality of valves in response to a sensor signal indicating oil debris in the oil flow, the plurality of valves determining the oil flow through an oil debris monitor sensor;
receiving a valve system configuration indicating a load applied to the plurality of valves;
generating, using a signal processor, a health indicator based on the oil debris indicated by the sensor signal and the load indicated by the valve system configuration; and
adjusting, via a controller, the valve system configuration using the control signals to control the plurality of valves to control the oil flow through the oil debris monitor sensor
wherein the plurality of valves comprises:
a bypass oil flow path that bypasses the oil debris monitor sensor;
an oil flow bypass valve connected in parallel with the oil debris monitor sensor, the oil flow bypass valve configured to control an amount of oil that flows through the bypass oil flow path; and
an oil flow regulator valve connected in series with the oil debris monitor sensor, the oil flow regulator valve configured to control an amount of input oil flow delivered to the oil debris monitor sensor.

14. The computer implemented method of claim 13, wherein the health indicator includes at least one of an estimated value of debris in the oil flow, a type of debris, a calculated size of debris particulate, and a calculated amount of debris in the oil over time.

15. The computer implemented method of claim 13, further comprising:
detecting, using an oil debris monitor sensor, oil debris by detecting one or more of at least a magnetic field and a disturbance to an expected magnetic field through the oil flow and calculating an oil debris amount that corresponds to the magnetic field detected.

16. The computer implemented method of claim 13, further comprising:
adjusting, using at least one of an oil flow bypass valve and regulator valve, the oil flow through at least one of the oil flow bypass valve and regulator valve to control the flow of the oil flow through an oil debris monitor sensor.

17. The computer implemented method of claim 13, further comprising:
adjusting, using an oil flow bypass valve, flow through the bypass valve based on at least one of a temperature of oil, pressure of oil, quantity of oil, opening and closing of other valves from the plurality of valves, oil flow through the oil debris monitor sensor, mechanical load, mode of operation, and shaft speeds.

18. A computer program product for oil debris monitoring in a gas turbine engine, the computer program product comprising a non-transitory computer readable storage medium having program instructions embodied therewith, the program instructions executable by a processor to cause the processor to:
generate control signals to control an oil flow using a plurality of valves in response to a sensor signal indicating oil debris in the oil flow, the plurality of valves determining the oil flow through an oil debris monitor sensor;
receive a valve system configuration indicating a load applied to the plurality of valves;
generate a health indicator based on the oil debris indicated by the sensor signal and the load indicated by the valve system configuration; and
adjusting, via a controller, the valve system configuration using the control signals to control the plurality of valves to control the oil flow through the oil debris monitor sensor,
wherein the plurality of valves comprises:
a bypass oil flow path that bypasses the oil debris monitor sensor;
an oil flow bypass valve connected in parallel with the oil debris monitor sensor, the oil flow bypass valve configured to control an amount of oil that flows through the bypass oil flow path; and
an oil flow regulator valve connected in series with the oil debris monitor sensor, the oil flow regulator valve configured to control an amount of input oil flow delivered to the oil debris monitor sensor.

* * * * *